United States Patent
Foster et al.

(10) Patent No.: US 8,419,848 B2
(45) Date of Patent: Apr. 16, 2013

(54) DISAZO COMPOUNDS AND THEIR USE IN INK-JET PRINTING

(75) Inventors: Clive Edwin Foster, Manchester (GB); David Phillip Devonald, Manchester (GB); Toshiki Fujiwara, Kanagawa (JP)

(73) Assignees: Fujifilm Imaging Colorants Limited, Manchester (GB); FUJIFILM Corporation, Tokyo (JP)

( * ) Notice: Subject to any disclaimer, the term of this patent is extended or adjusted under 35 U.S.C. 154(b) by 190 days.

(21) Appl. No.: 13/122,840

(22) PCT Filed: Oct. 8, 2009

(86) PCT No.: PCT/GB2009/051332
§ 371 (c)(1),
(2), (4) Date: Apr. 6, 2011

(87) PCT Pub. No.: WO2010/041065
PCT Pub. Date: Apr. 15, 2010

(65) Prior Publication Data
US 2011/0200800 A1    Aug. 18, 2011

(30) Foreign Application Priority Data
Oct. 10, 2008    (GB) .................................. 0818567.0

(51) Int. Cl.
*C09D 11/02* (2006.01)
*C09B 31/14* (2006.01)

(52) U.S. Cl.
USPC ....................................... 106/31.48; 534/757

(58) Field of Classification Search ............... 106/31.48, 106/31.5; 534/757; 347/100; 428/195.1
See application file for complete search history.

(56) References Cited

U.S. PATENT DOCUMENTS

| | | | | |
|---|---|---|---|---|
| 4,124,581 A * | 11/1978 | Vor der Bruck et al. | ...... | 534/757 |
| 4,908,435 A * | 3/1990 | Gregory | ........................ | 534/757 |
| 7,083,670 B2 * | 8/2006 | Takasaki et al. | ........... | 106/31.48 |
| 7,186,292 B2 * | 3/2007 | Yabuki et al. | .............. | 106/31.48 |
| 7,192,475 B2 * | 3/2007 | Takasaki et al. | ............. | 106/31.5 |
| 7,250,079 B2 * | 7/2007 | Chino et al. | ................ | 106/31.48 |
| 7,402,201 B2 * | 7/2008 | Wachi et al. | ............... | 106/31.48 |
| 7,431,760 B2 | 10/2008 | Chino et al. | ............... | 106/31.48 |
| 7,465,346 B2 | 12/2008 | Fukumoto et al. | ......... | 106/31.48 |
| 7,491,266 B2 | 2/2009 | Taguchi et al. | ............ | 106/31.27 |
| 7,533,978 B2 * | 5/2009 | Chino et al. | .................. | 347/100 |
| 2011/0195236 A1 * | 8/2011 | Foster et al. | ............... | 106/31.48 |
| 2011/0200800 A1 * | 8/2011 | Foster et al. | ............... | 428/195.1 |

FOREIGN PATENT DOCUMENTS

| | | |
|---|---|---|
| EP | 1 518 907 | 3/2005 |
| EP | 1 553 147 | 7/2005 |
| WO | WO 2009/101428 | 8/2009 |
| WO | WO 2010/041066 | 4/2010 |

OTHER PUBLICATIONS

International Search Report and Written Opinion issued Nov. 30, 2009, in PCT Application No. PCT/GB2009/051332.

* cited by examiner

*Primary Examiner* — Helene Klemanski
(74) *Attorney, Agent, or Firm* — Morgan, Lewis & Bockius LLP

(57) ABSTRACT

A compound of Formula (1) or a salt thereof:

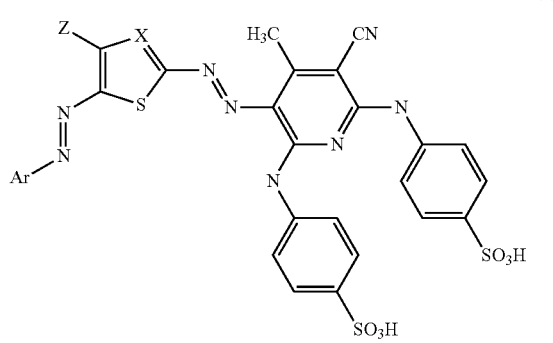

Formula (1)

wherein:
X is N or C(CN);
Z is optionally substituted naphthyl; and
Ar is an aryl group carrying at least one nitro substituent and optionally one or more further substituents.

17 Claims, No Drawings

DISAZO COMPOUNDS AND THEIR USE IN INK-JET PRINTING

This application is a 371 filing based on PCT/GB2009/051332, filed Oct. 8, 2009, which claims priority to United Kingdom Application No. 0818567.0, filed Oct. 10, 2008, all of which are hereby incorporated by reference in their entirety.

This invention relates to compounds, compositions and inks, to printing processes, to printed materials and to ink-jet printer cartridges.

Ink-jet printing is a non-impact printing technique in which droplets of ink are ejected through a fine nozzle onto a substrate without bringing the nozzle into contact with the substrate. The set of inks used in this technique typically comprise yellow, magenta, cyan and black inks.

With the advent of high-resolution digital cameras and ink-jet printers it is becoming increasingly common for consumers to print photographs using an ink-jet printer.

While ink-jet printers have many advantages over other forms of printing and image development there are still technical challenges to be addressed. For example, there are the contradictory requirements of providing ink colorants that are soluble in the ink medium and yet display excellent wet-fastness (i.e. prints do not run or smudge when exposed to water). The inks also need to dry quickly to avoid sheets sticking together after they have been printed, but they should not crust over the tiny nozzles used in the printer. Storage stability is also important to avoid particle formation that could block the nozzles in the print-head especially since consumers can keep an ink-jet ink cartridge for several months. Furthermore, and especially important with photographic quality reproductions, the resultant images should not fade rapidly on exposure to light or ozone. It is also desirable that the shade and chroma of the colorant are within a narrow tolerance so that an image may be optimally reproduced.

Thus, developing new colorants for ink-jet printing presents a unique challenge in balancing all these conflicting and demanding properties.

The present invention aims to provide colorants especially suited for use in ink jet printing inks which are improved in respect of one or more of the above properties.

According to a first aspect of the present invention there is provided a compound of Formula (1) or a salt thereof:

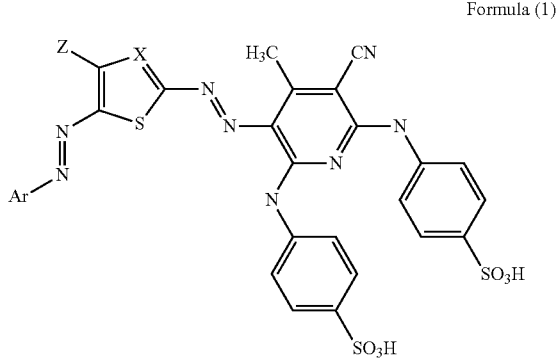

Formula (1)

wherein:
X is N or C(CN);
Z is optionally substituted alkyl, optionally substituted aryl or optionally substituted heterocyclyl; and
Ar is an aryl group carrying at least one nitro substituent and optionally one or more further substituents.

Z

Preferably Z is optionally substituted $C_{1-12}$-alkyl (especially optionally substituted $C_{1-4}$-alkyl), optionally substituted phenyl or optionally substituted naphthyl.

It is particularly preferred that Z is optionally substituted naphthyl. We have found that Compounds of Formula (1) and salts thereof wherein Z is optionally substituted naphthyl tend to have even better overall properties for ink jet printing.

In particular we have found these compounds tend to provide prints having even better light and/or ozone fastness. Whilst not wishing to be limited by theory we speculate that the combination of:
(i) the at least one nitro group on the Ar group; and
(ii) the naphthyl group for Z;
provides particularly good properties including ozone fastness.

When Z is optionally substituted naphthyl the naphthyl is preferably attached in the 2-position.

Preferably, Z is an unsubstituted naphthyl group. These compounds tend to have even better ozone fastness.

Optional Substituents for Z

Optional substituents which may be present on Z are preferably selected from:
optionally substituted alkoxy (preferably $C_{1-4}$-alkoxy),
optionally substituted aryl (preferably phenyl),
optionally substituted aryloxy (preferably phenoxy),
optionally substituted heterocyclyl (preferably heteroaryl), preferred examples of which include 5- and 6-membered rings contain 1 or 2 hetero atoms selected from N, S and P;
polyalkylene oxide (preferably polyethylene oxide or polypropylene oxide), phosphato (especially phosphoric acid or phosphonic acid), nitro, sulfo (especially sulfonic acid), cyano, halo, ureido, hydroxy, ester (including sulfate and phosphate esters and especially carboxyester), sulfone,
—$NR^aR^b$, —$COR^a$, —$CONR^aR^b$, —$NHCOR^a$, and —$SO_2NR^aR^b$, wherein $R^a$ and $R^b$ are each independently H, optionally substituted alkyl (especially $C_{1-4}$-alkyl), optionally substituted aryl or optionally substituted heteroaryl.

When Z is aryl, aryloxy or heterocyclyl it may also carry optionally substituted alkyl (especially $C_{1-4}$-alkyl) substituents.

When present the optional substituents on the optionally substituted alkoxy, aryl, aryloxy, heterocyclyl and alkyl groups (as motioned above in respect of the Z group) may be selected from halo, amino, nitro, cyano, hydroxy, sulfonic acid, carboxylic acid and phosphonic acid groups.

When present, halo is preferably Cl, Br or F.

Preferred optional substituents for Z are water solubilising groups especially carboxy, sulfo (especially sulfonic acid) and phosphato (especially phosphonic acid) and more especially carboxy and sulfo.

Ar

Preferably Ar is phenyl carrying at least one nitro substituent and optionally one or more further substituents or Ar is naphthyl carrying at least one nitro substituent and one or more further substituents. More preferably Ar is naphthyl carrying at least one nitro substituent and one or more further substituents. When Ar is naphthyl it is preferably attached in the 2-position.

Nitro Groups on Ar

Preferably Ar carries from 1 to 3 nitro groups, more preferably 1 (i.e. only 1) nitro group.

Preferably, when Ar is naphthyl it has the Formula:

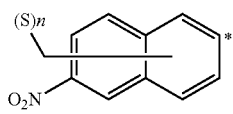

wherein:
  each S group independently is an optional substituent as described above for the Z group;
  n is from 1 to 3 (preferably 2); and
  the asterisk (*) represents the point of attachment to the azo linkage in the compound of Formula (1) or a salt thereof.

Preferably, each S group is a water solubilising group as described above. Especially preferably each S groups is selected from carboxy (especially carboxylic acid) and sulfo (especially sulfonic acid) groups.

Most especially Ar is of the Formula:

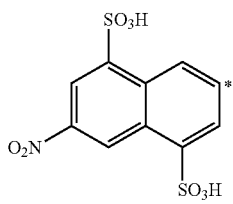

wherein the asterisk (*) represents the point of attachment to the azo linkage in the compound of Formula (1) or a salt thereof.

Optional Further Substituents on Ar

Optional further substituents which may be present on Ar are selected from:
  optionally substituted alkyl (especially $C_{1-4}$-alkyl);
  optionally substituted alkoxy (preferably $C_{1-4}$-alkoxy),
  optionally substituted aryl (preferably phenyl),
  optionally substituted aryloxy (preferably phenoxy),
  optionally substituted heterocyclyl (especially heteroaryl),
  polyalkylene oxide (preferably polyethylene oxide or polypropylene oxide), phosphato (especially phosphoric acid or phosphonic acid), sulfo (especially sulfonic acid), cyano, halo, ureido, hydroxy, ester (including sulfate and phosphate esters and especially carboxyester), sulfone,
  —$NR^aR^b$, —$COR^a$, —$CONR^aR^b$, —$NHCOR^a$ and —$SO_2NR^aR^b$, wherein $R^a$ and $R^b$ are each independently H, optionally substituted alkyl (especially $C_{1-4}$-alkyl), optionally substituted aryl or optionally substituted heteroaryl.

When present the optional substituents on the optionally further substituted alkyl, alkoxy, aryl, aryloxy and heterocyclyl (as motioned above in respect of the Ar group) may be selected from halo, amino, nitro, cyano, hydroxy, sulfonic acid, carboxylic acid and phosphonic acid groups.

Preferred optional substituents for Ar are water solubilising groups. Preferred water solubilising groups include hydroxy, polyethyleneoxy, carboxy (carboxylic acid), sulfo (especially sulfonic acid) and phosphato (especially phosphonic acid). Of these carboxy and sulfo are especially preferred.

Preferably, Ar carries at least one water solubilising group. More preferably Ar carries from 1 to 3 water solubilising groups and especially 2 water solubilising groups.

Fibre Reactive Groups

The compounds of Formula (1) or salts thereof are also preferably free from fibre reactive groups. The term fibre reactive group is well known in the art and is described for example in EP 0356014 A1. Fibre reactive groups are capable, under suitable conditions, of reacting with the hydroxy groups present in cellulosic fibres or with the amino groups present in natural fibres to form a covalent linkage between the fibre and the dye. As examples of fibre reactive groups excluded from the compounds of Formula (1) there may be mentioned aliphatic sulfonyl groups which contain a sulfate ester group in beta-position to the sulfur atom, e.g. beta-sulfato-ethylsulfonyl groups, alpha, beta-unsaturated acyl radicals of aliphatic carboxylic acids, for example acrylic acid, alpha-chloro-acrylic acid, alpha-bromoacrylic acid, propiolic acid, maleic acid and mono- and dichloro maleic; also the acyl radicals of acids which contain a substituent which reacts with cellulose in the presence of an alkali, e.g. the radical of a halogenated aliphatic acid such as chloroacetic acid, beta-chloro and beta-bromopropionic acids and alpha, beta-dichloro- and dibromopropionic acids or radicals of vinylsulfonyl- or beta-chloroethylsulfonyl- or beta-sulfatoethyl-sulfonyl-endo-methylene cyclohexane carboxylic acids. Other examples of cellulose reactive groups are tetrafluorocyclobutyl carbonyl, trifluoro-cyclobutenyl carbonyl, tetrafluorocyclobutylethenyl carbonyl, trifluoro-cyclobutenylethenyl carbonyl; activated halogenated 1,3-dicyanobenzene radicals; and heterocyclic radicals which contain 1, 2 or 3 nitrogen atoms in the heterocyclic ring and at least one cellulose reactive substituent on a carbon atom of the ring, for example a triazinyl halide.

It will be appreciated that all of above mentioned preferred substituents are not fibre reactive groups.

Salts

When acid or basic groups (particularly acid groups) are present in the compounds of Formula (1) they are preferably in the form of a salt. Thus, all Formulae shown herein include the compounds in salt form.

Preferred salts are alkali metal salts, especially lithium, sodium and potassium; ammonium and substituted ammonium salts (including quaternary amines such as $((CH_3)_4N^+)$ and mixtures thereof. Especially preferred are salts with sodium, lithium, ammonia and volatile amines. More especially it is preferred that the compound of Formula (1) comprise a lithium salt. Preferably, the compounds of Formula (1) is in the form of a lithium salt. Compounds of Formula (1) may be converted into a salt using known techniques.

The compounds of Formula (1) and salts thereof may exist in tautomeric forms other than those shown in this specification. These tautomers are included within the scope of the present invention and its claims.

Preferred Compounds of Formula (1)

Preferred compounds of Formula (1) and salts thereof include those of Formulae (2) to (4) and salts thereof:

Formula (2)

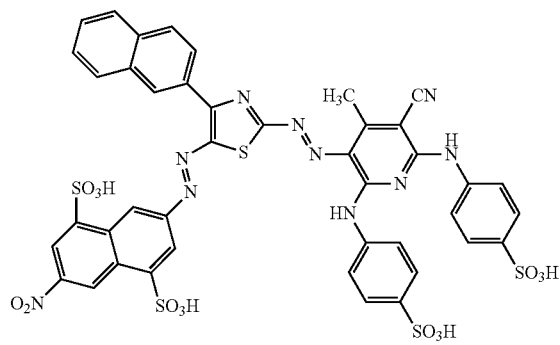

Formula (3)

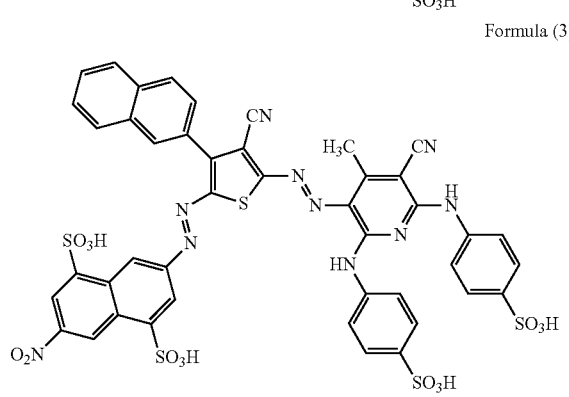

Formula (4)

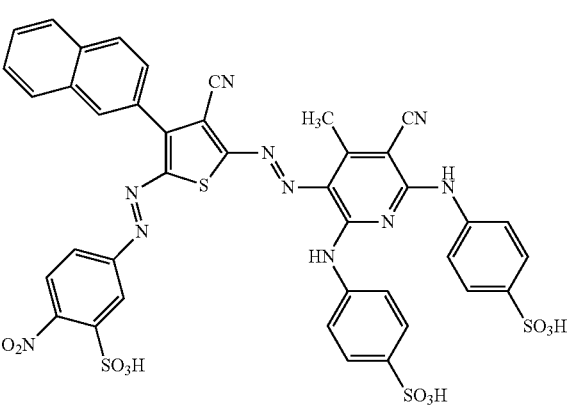

The above compounds of Formulae (2) to (4) have been found to display, among other things, especially good ozone fastness.

Preferably, the compounds of Formulae (2) to (4) or a salt thereof are in the form of the lithium salt.

Synthesis

The compounds of Formula (1) or salts thereof may be prepared by any method known in the art, and particularly by processes such as those described in U.S. Pat. No. 7,192,475 which is incorporated herein by reference. The compounds of Formula (1) or salts thereof described herein can be synthesised by methods known in the art. For example, an aryl amine may be diazotised under aqueous conditions with sodium nitrite and hydrochloric acid. The diazotised aryl amine may then be added to a solution or suspension of a cyano substituted thiophene amine or a thiazole amine. Sometimes, a miscible organic solvent such as methanol or N-methyl-2-pyrrolidone can be used as a cosolvent in conjunction with water. The resulting monoazo compound, once isolated, can be reacted with a pyridine-based coupler in a manner that ensures diazotisation and coupling occur in situ. For this coupling step it may be advantageous to use for example isoamyl nitrite.

Alternatively, a step-wise synthetic method can be used, for example the monoazo compound may be diazotised prior to the coupling reaction.

To introduce the required nitro group Nitrosyl sulfuric acid is a suitable nitrosating agent. Amine groups can be projected from the nitrosating agent by using for example acetyl protecting groups. The acetyl protecting groups can be later removed by acidic or basic hydrolysis.

One suitable synthetic method is described schematically as indicated below:

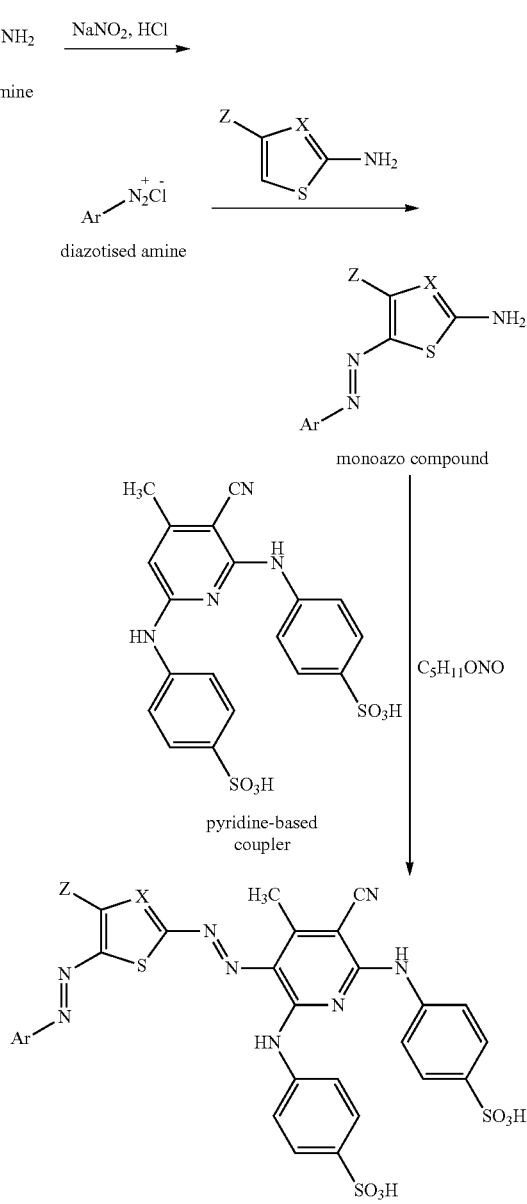

wherein Ar, X and Z are as hereinbefore defined.

The compounds of Formula (1) are valuable colorants for use in the preparation of ink-jet printing inks especially black ink-jet printing inks. They benefit from a good balance of solubility, storage stability and fastness to water, ozone and light. In particular they display excellent ozone fastness.

Compositions and Inks

According to a second aspect of the present invention there is provided a composition comprising a compound of Formula (1) or a salt thereof according to the first aspect of the invention and a liquid medium.

Preferred compositions according to the second aspect of the invention comprise:
(a) from 0.01 to 30 parts of a compound of Formula (1) or a salt thereof according to the first aspect of the present invention; and
(b) from 70 to 99.99 parts of a liquid medium;
wherein all parts are by weight.

Preferably, the number of parts of (a)+(b)=100.

The number of parts of component (a) is preferably from 0.1 to 20, more preferably from 0.5 to 15, and especially from 1 to 5 parts. The number of parts of component (b) is preferably from 80 to 99.9, more preferably from 85 to 99.5 and especially from 95 to 99 parts.

Preferably component (a) is completely dissolved in component (b). Preferably component (a) has a solubility in component (b) at 20° C. of at least 1% by weight, more preferably at least 2%, especially at least 5% and most especially at least 10% by weight. This allows the preparation of liquid dye concentrates that may be used to prepare more dilute inks and reduces the chance of the dye precipitating if evaporation of the liquid medium occurs during storage. Preferably, the liquid medium for establishing the required solubility is water.

Thus, the present invention also provides a composition (preferably an ink) where component (a) is present in an amount of 2.5 to 7 parts, more preferably 2.5 to 5 parts (a high concentration ink) or component (a) is present in an amount of 0.5 to 2.4 parts, more preferably 0.5 to 1.5 parts (a low concentration ink).

Preferred liquid media include water, a mixture of water and organic solvent and organic solvent free from water. Preferably, the liquid medium comprises a mixture of water and organic solvent or organic solvent free from water.

When the liquid medium (b) comprises a mixture of water and organic solvent, the weight ratio of water to organic solvent is preferably from 99:1 to 1:99, more preferably from 99:1 to 50:50, especially from 99:1 to 70:30 and most especially from 95:5 to 80:20.

It is preferred that the organic solvent present in the mixture of water and organic solvent is a water-miscible organic solvent or a mixture of such solvents. Preferred water-miscible organic solvents include $C_{1-6}$-alkanols, preferably methanol, ethanol, n-propanol, isopropanol, n-butanol, sec-butanol, tert-butanol, n-pentanol, cyclopentanol and cyclohexanol; linear amides, preferably dimethylformamide or dimethylacetamide; ketones and ketone-alcohols, preferably acetone, methyl ether ketone, cyclohexanone and diacetone alcohol; water-miscible ethers, preferably tetrahydrofuran and dioxane; diols, preferably diols having from 2 to 12 carbon atoms, for example ethylene glycol, propylene glycol, butylene glycol, pentylene glycol, hexylene glycol and thiodiglycol and oligo- and poly-alkyleneglycols, preferably diethylene glycol, triethylene glycol, polyethylene glycol and polypropylene glycol; triols, preferably glycerol and 1,2,6-hexanetriol; mono-$C_{1-4}$-alkyl ethers of diols, preferably mono-$C_{1-4}$-alkyl ethers of diols having 2 to 12 carbon atoms, especially 2-methoxyethanol, 2-(2-methoxyethoxy)ethanol, 2-(2-ethoxyethoxy)-ethanol, 2-[2-(2-methoxyethoxy) ethoxy]ethanol, 2-[2-(2-ethoxyethoxy)-ethoxy]-ethanol and ethyleneglycol monoallylether; cyclic amides, preferably 2-pyrrolidone, N-methyl-2-pyrrolidone, N-ethyl-2-pyrrolidone, caprolactam and 1,3-dimethylimidazolidone; cyclic esters, preferably caprolactone; sulfoxides, preferably dimethyl sulfoxide; and sulfones, preferably sulfolane. Preferably the liquid medium comprises water and 1 or more, especially from 2 to 8, water-miscible organic solvents.

Especially preferred water-miscible organic solvents are cyclic amides, especially 2-pyrrolidone, N-methyl-pyrrolidone and N-ethyl-pyrrolidone; diols, especially 1,5-pentane diol, ethyleneglycol, thiodiglycol, diethyleneglycol and triethyleneglycol; and mono-$C_{1-4}$-alkyl and $C_{1-4}$-alkyl ethers of diols, more preferably mono-$C_{1-4}$-alkyl ethers of diols having 2 to 12 carbon atoms.

When the liquid medium comprises organic solvent free from water, (i.e. less than 1% water by weight) the solvent preferably has a boiling point of from 30 to 200° C., more preferably of from 40 to 150° C., especially from 40 to 125° C. The organic solvent may be water-immiscible, water-miscible or a mixture of such solvents. Preferred water-miscible organic solvents are any of the hereinbefore-described water-miscible organic solvents and mixtures thereof. Preferred water-immiscible solvents include, for example, aliphatic hydrocarbons; esters, preferably ethyl acetate; chlorinated hydrocarbons, preferably $CH_2Cl_2$; and ethers, preferably diethyl ether; and mixtures thereof.

When the liquid medium comprises a water-immiscible organic solvent, preferably a polar solvent is included because this enhances solubility of the mixture of dyes in the liquid medium. Examples of polar solvents include $C_{1-4}$-alcohols and ketones.

In view of the foregoing preferences it is especially preferred that where the liquid medium is organic solvent free from water it comprises a ketone (especially methyl ethyl ketone) and/or an alcohol (especially a $C_{1-4}$-alkanol, more especially ethanol or propanol).

The organic solvent free from water may be a single organic solvent or a mixture of two or more organic solvents. It is preferred that when the liquid medium is organic solvent free from water it is a mixture of 2 to 5 different organic solvents. This allows a liquid medium to be selected that gives good control over the drying characteristics and storage stability of the ink.

Liquid media comprising organic solvent free from water are particularly useful where fast drying times are required and particularly when printing onto hydrophobic and non-absorbent substrates, for example plastics, metal and glass.

The liquid media may of course contain additional components suitable for use in ink-jet printing inks, for example viscosity and surface tension modifiers, corrosion inhibitors, biocides, kogation reducing additives and surfactants which may be ionic or non-ionic.

Colour Blends

The compositions and inks described above may contain one compound of Formula (1) or a salt thereof or a mixture of two or more compounds of Formula (1) or salts thereof.

Optionally, further colorant(s) (not of Formula (1) or a salt thereof) may be added to the composition or ink to modify the shade and performance properties. They may also be added to adjust the cost:performance ratio.

The further colorant(s) may be of any colour (including cyan, magenta, yellow and especially black). Preferably, the further colorant are themselves suitable for ink jet printing inks. Further colorants may be selected from those listed in the Colour Index, and salts thereof, and those commercially available specifically for ink-jet printing. The further colorants may be pigments but more preferably they are dyes and especially water soluble dyes.

Preferably, the further colorants are selected from those disclosed in U.S. Pat. Nos. 7,491,266, and 7,533,978, the examples of which are incorporated herein by reference.

Suitable further black colorants include C.I. Food Black 2, C.I. Direct Black 19, C.I. Reactive Black 31, PRO-JET™ Fast Black 2, C.I. Direct Black 195; C.I. Direct Black 168; and black dyes described in patents by Lexmark (e.g. EP 0539178 A2, Examples 1, 2, 3, 4 and 5) and Orient Chemicals (e.g. EP 0347803 A2, pages 5-6, azo dyes 3, 4, 5, 6, 7, 8, 12, 13, 14, 15 and 16)

Suitable further magenta colorants include PRO-JET™ Fast Magenta 2.

Suitable further yellow colorants include C.I. Direct Yellow 142; C.I. Direct Yellow 132; C.I. Direct Yellow 86; C.I. Direct Yellow 85; C.I. Direct Yellow 173; and C.I. Acid Yellow 23.

Suitable further cyan colorants include phthalocyanine colorants, e.g. Direct Blue 199 and Acid Blue 99.

It will be appreciated that the compositions and inks described above may be used as the black ink in a colour printing ink set. Suitable colorants for the magenta, yellow and cyan inks in the set are well known in the arts and can be chosen readily from any of those disclosed in the art or commercially available. The further magenta, yellow and cyan colorants described above may be used to prepared the yellow, magenta and cyan inks in the ink set.

It is preferred that the composition according to the second aspect of the present invention is an ink suitable for use in an ink-jet printer. Such a composition may also be referred to herein simply as an "ink jet printer ink". Ink suitable for use in an ink-jet printer is ink which is preferably able to repeatedly fire through an ink-jet printing head without causing blockage of the fine nozzles. To do this the ink is preferably substantially free of particles of a size above 1 micron in diameter, stable (i.e. does not precipitate on storage) and has a viscosity which allows for good droplet formation at the print head. For thermal ink jet printer inks it is also preferred that the composition is substantially free from metal corrosive components such as chloride ions.

Ink suitable for use in an ink-jet printer preferably has a viscosity of less than 30 cP, more preferably less than 20 cP, especially less than 10 cP and most especially less than 5 cP, at 25° C. 1 cP equals 1 mPa·s.

Ink suitable for use in an ink-jet printer preferably contains less than 500 ppm, more preferably less than 250 ppm, especially less than 100 ppm, more especially less than 10 ppm in total of divalent and trivalent metal ions (other than any divalent and trivalent metal ions bound to a compound of Formula (1) or any other colorant or additive incorporated in the ink).

Preferably, ink suitable for use in an ink-jet printer has been filtered through a filter having a mean pore size below 10 μm, more preferably below 3 μm, especially below 2 μm, more especially below 1 μm. This filtration removes particulate matter that could otherwise block the fine nozzles found in many ink-jet printers.

Preferably, ink suitable for use in an ink-jet printer contains less than 500 ppm, more preferably less than 250 ppm, especially less than 100 ppm, more especially less than 10 ppm in total of halide ions.

Printing Process

According to a third aspect of the present invention there is provided a process for forming an image on a substrate comprising ink jet printing a composition according to the second aspect of the present invention which is suitable for use in an ink-jet printer (an ink jet printer ink) to the substrate.

The ink-jet printer preferably applies the ink to the substrate in the form of droplets that are ejected through a small orifice onto the substrate. Preferred ink-jet printers are piezoelectric ink-jet printers and thermal ink-jet printers. In thermal ink-jet printers, programmed pulses of heat are applied to the ink in a reservoir by means of a resistor adjacent to the orifice, thereby causing the ink to be ejected from the orifice in the form of small droplets directed towards the substrate during relative movement between the substrate and the orifice. In piezoelectric ink-jet printers the oscillation of a small crystal causes ejection of the ink from the orifice. Alternately the ink can be ejected by an electromechanical actuator connected to a moveable paddle or plunger, for example as described in International Patent Application WO00/48938 and International Patent Application WO00/55089.

The substrate is preferably paper, plastic, a textile, metal or glass, more preferably paper, an overhead projector slide or a textile material, especially paper.

Preferred papers are plain or treated papers which may have an acid, alkaline or neutral character. Photographic quality papers are especially preferred. In some embodiments the paper may have an ink jet receptor coating which may be porous or swellable.

Printed Material (Substrate)

According to a fourth aspect of the present invention there is provided a material (substrate) printed with a compound or a salt thereof according to the first aspect of the present invention, a composition according to the second aspect of the invention or by means of a process according to the third aspect of the invention.

The material used is preferably paper, plastic, a textile, metal or glass, more preferably paper, an overhead projector slide or a textile material, especially paper more especially plain, coated or treated papers It is especially preferred that the printed material of the fourth aspect of the invention is a print on a photographic quality paper printed using a process according to the third aspect of the present invention.

According to a fifth aspect of the present invention there is provided an ink-jet printer cartridge comprising a chamber and a composition according to the second aspect of the present invention which is suitable for use in an ink-jet printer, wherein the composition is in the chamber.

The invention is further illustrated by the following Examples in which all parts and percentages are by weight unless otherwise stated.

EXAMPLE 1

Preparation of the Lithium Salt of

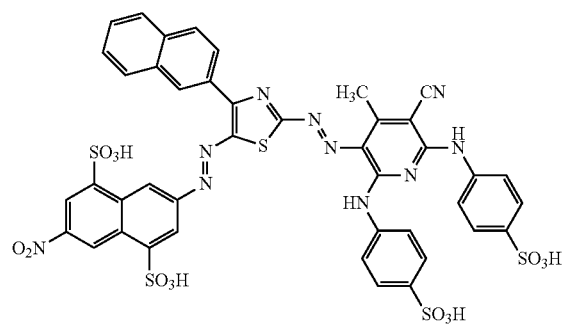 [SMILES: Cc1c(C#N)c(Nc2ccc(S(=O)(=O)O)cc2)nc(Nc2ccc(S(=O)(=O)O)cc2)c1/N=N/c1nc(-c2ccc3ccccc3c2)c(/N=N/c2cc(S(=O)(=O)O)c3cc([N+](=O)[O-])cc(S(=O)(=O)O)c3c2)s1]

Stage 1a

Preparation of

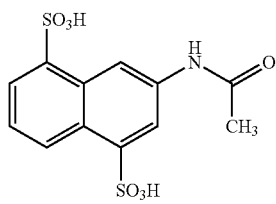 [SMILES: CC(=O)Nc1cc(S(=O)(=O)O)c2cccc(S(=O)(=O)O)c2c1]

2-Naphthylamine-4,8-disulfonic acid (Cassella acid) (supplied by TCI, 0.272 mol) was stirred in water at pH 7 to form a solution. Acetic anhydride (27.72 g: 0.272 mol) was added to the solution over the course of 10 minutes at a temperature of less than 25° C. whist maintaining a pH of 7 by the addition of 2M sodium hydroxide. This formed a reaction mixture The reaction mixture was stirred overnight at a temperature of 25° C. and then adjusted to pH 1 by the addition of concentrated hydrochloric acid. The product which precipitated was collected by filtration and washed with 20% sodium chloride solution. The precipitate was stirred with acetone, collected by filtration and the treatment repeated. The resulting product was dried in an oven to give a solid (105.41 g).

Stage 1b

Preparation of

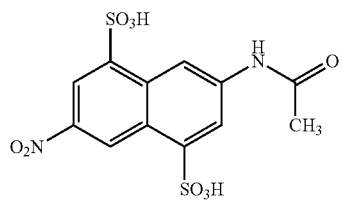 [SMILES: CC(=O)Nc1cc(S(=O)(=O)O)c2cc([N+](=O)[O-])cc(S(=O)(=O)O)c2c1]

The product of stage 1a (0.20 mol) was added to stirred sulfuric acid SG1.84 at a temperature below 20° C. over the course of 1 hour and then stirred at 25° C. for 6 hours. A mixed acid composition (24.18% of 20% oleum, 50.44% of 95% sulfuric acid and 25.38% of 95% nitric acid) (52.84 g) was then added drop-wise over 40 minutes at a temperature of less than 5° C. This formed a reaction mixture. The reaction mixture was then allowed to warm to 25° C. whilst stirring overnight. The next day the reaction mixture was drowned into ice and stirred for 2 hours. The product was precipitated by the addition of magnesium sulfate, collected by filtration and washed with 20% magnesium sulfate solution to give a damp paste.

Stage 1c

Preparation of

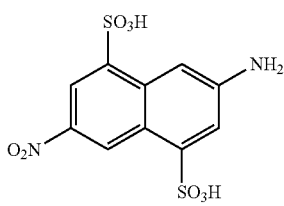 [SMILES: Nc1cc(S(=O)(=O)O)c2cc([N+](=O)[O-])cc(S(=O)(=O)O)c2c1]

The damp paste from stage 1b (0.4 mol) was stirred in approx 1M sulfuric acid (650 ml) at 75° C. for 2.5 hours to form a reaction mixture. The reaction mixture was allowed to cool to 25° C. which caused precipitation. The precipitate was collected by filtration, and washed with acetone. The resulting product was dried to give an orange solid 66.5 g.

Stage 1d

Preparation of

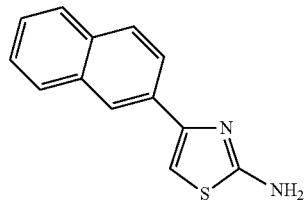 [SMILES: Nc1nc(-c2ccc3ccccc3c2)cs1]

This intermediate was purchased from Aesar.

Stage 1e

Preparation of

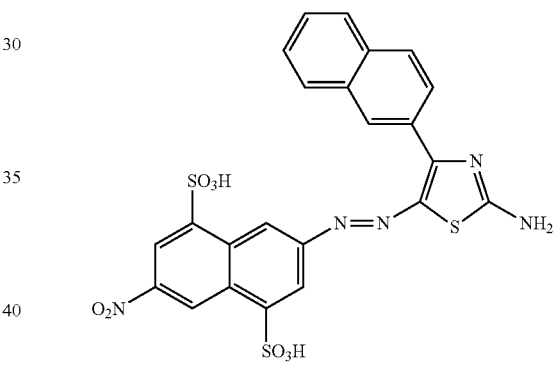

3-Amino-7-nitronaphthalene-1,5-disulfonic acid (from stage 1c) (0.026 mol) was dissolved with stirring in water (200 ml) at pH 8, cooled to 4° C. and then concentrated hydrochloric acid (10 ml) was added. A solution of sodium nitrite (1.8 g; 0.0261 mol) in water (20 ml)) was added drop-wise at 0-5° C. After stirring for 1 hour at 0-5° C. the excess nitrous acid was destroyed by the addition of sulfamic acid. The resulting diazonium salt was added drop-wise at a temperature of less than 10° C. to a stirred solution of the intermediate purchased in stage 1d (4.98 g; 0.022 mol) in methanol (300 ml), N-methylpyrrolidin-2-one (50 ml) and lithium acetate (5 g). This formed a reaction mixture. The reaction mixture was then warmed to 25° C. After stirring overnight at 25° C. and a pH of 5.7 the pH was then adjusted to a pH of about 1 by the addition of 2M hydrochloric acid, the product was collected by filtration, washed with acetone (200 ml) and then dried in an oven to give a red solid 13.18 g. Mass spectrometry showed the product of stage 1e had a mass spectrum (ES−) 584 [M-H]⁻, 292 [M-2H]²⁻.

Stage 1f

Preparation of the Title Compound

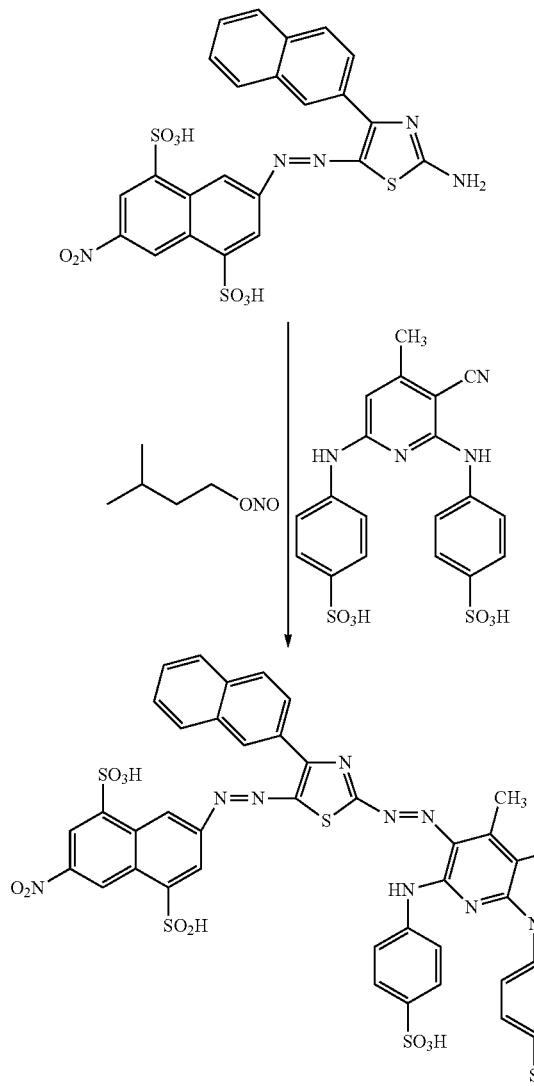

The monoazo product of stage 1e (0.062 mol) and pyridine coupler (0.074 mol) (prepared as described in EP1553147 and JP-A-2003-306623) were combined in water at 38° C. and isoamyl nitrite (1.65 ml:0.0123 mol) was added. The resulting mixture was stirred for 1.5 hours at 38-57° C., cooled to 10° C., diluted with propan-2-ol (800 ml), filtered and then the collected solid was washed with propan-2-ol. The resulting solid was dissolved in water at pH 6-7, salted out with lithium chloride, warmed to 60° C. and propan-2-ol (200 ml) added. The resulting mixture was allowed to cool to room temperature and then collected by filtration. The resulting damp paste was dissolved in water at pH 8, dialysed using Visking™ tubing (to a conductivity of less than 30 μScm$^{-1}$) and then filtered (GF/A, 0.45 μm nylon). The resulting solution was dried in an oven to give a reddish black solid 3.00 g as the final product. The compound of Example 1 had a lambda max in water of 615 nm and an extinction coefficient of 34,000.

EXAMPLE 2

Preparation of the Lithium Salt of

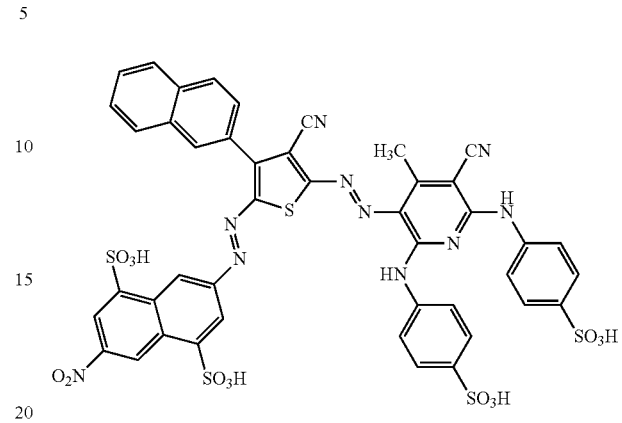

The compound of Example 2 was prepared in exactly the same way as in Example 1 except that the intermediate of stage 1d was replaced with intermediate 2d in the same molar amounts:

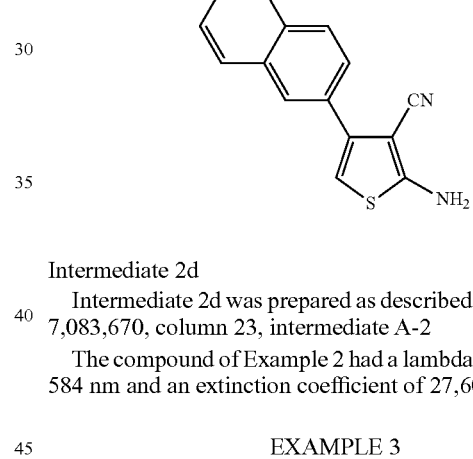

Intermediate 2d

Intermediate 2d was prepared as described in U.S. Pat. No. 7,083,670, column 23, intermediate A-2

The compound of Example 2 had a lambda max in water of 584 nm and an extinction coefficient of 27,600.

EXAMPLE 3

Preparation of the Lithium Salt of

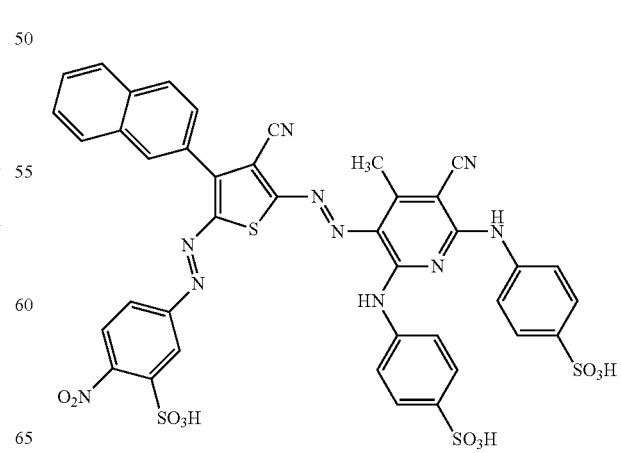

Stage 3a

Preparation of

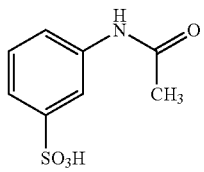

The desired intermediate 3a was prepared by the acetylation of metanilic acid (supplied by Acros) using the acetylation protocol as described in stage 1a.

Stage 3b

Preparation of

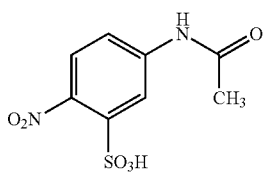 [SMILES: CC(=O)Nc1ccc([N+](=O)[O-])c(S(=O)(=O)O)c1]

Acetyl metanilic (from stage 3a) (254 g; 1 mol) was added to sulfuric acid SG1.84 (1500 g) with stirring at a temperature of less than 5° C. over the course of 1 hour. After stirring for a further 2 hours a mixture of 70% nitric acid SG1.42 (90 g) in sulfuric acid (90 g) was added over the course of 1 hour at a temperature of less than 5° C. The resulting mixture was stirred overnight, warming to 25° C. The next day the mixture was poured into ice (2 kg) and then allowed to warm to 25° C. The precipitated product was collected by filtration to give a damp paste.

Stage 3c

Preparation of

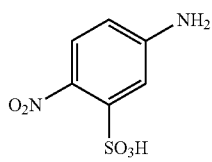 [SMILES: Nc1ccc([N+](=O)[O-])c(S(=O)(=O)O)c1]

The damp paste from stage 3b was stirred in 2M sodium carbonate (1,000 ml) and heated to reflux for 3 hours. Upon cooling to 25° C. the product was collected by filtration and the damp paste stirred in acetone (2,000 ml). The resulting product was dried to give a solid (132.7 g).

Stage 3d

Preparation of the Title Compound

The title compound was prepared as in Example 1 except that the intermediate of stage 1d was replaced by the intermediate 2d as described in Example 2 and the intermediate of stage 1c was replaced with the intermediate of stage 3c. The intermediate compounds 2d and 3c were used in the same molar amounts as 1d and 1c respectively. The compound of Example 3 had a lambda max in water of 561 nm and an extinction coefficient of 33,400.

Comparative Dye

The comparative dye was the lithium salt of Example D41 in U.S. Pat. No. 7,192,475:

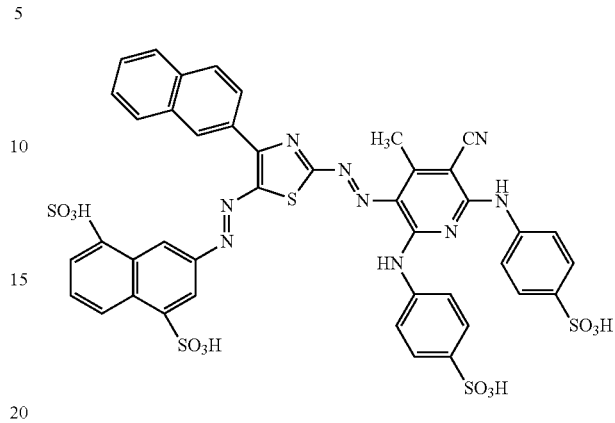

Preparation of Inks

Inks were prepared by dissolving 3 parts by weight of the dye of Example 1, 2, or the Comparative Dye in 97 parts by weight of a liquid medium comprising % by weight:

| | |
|---|---|
| Diethylene glycol | 7% |
| Ethylene glycol | 7% |
| 2-Pyrollidone | 7% |
| Surfynol ™ 465 | 1% |
| Tris buffer | 0.2% |
| Water | 77.8% | and adjusting the pH of the ink to 8-8.5 using aqueous sodium hydroxide solution.

Surfynol® 465 is a surfactant from Air Products.

Tris buffer comprises tris(hydroxymethyl)aminomethane.

The inks were prepared and referenced according to Table 1.

TABLE 1

| Example dye | Ink Example |
|---|---|
| Example 1 | Ink 1 |
| Example 2 | Ink 2 |
| Comparative dye | C. Ink 1 |

Ink-Jet Printing

The Inks prepared as described above were filtered through a 0.45 micron nylon filter and then incorporated into empty print cartridges using a syringe.

The inks were each ink jet printed on to Canon Professional Photo Paper™ (PR101) and Epson Crispia™ paper.

Print Testing

The prints were tested for ozone fastness by exposure to 5 ppm ozone at 25° C., 50% relative humidity for 24 hours in a Hampden 903 Ozone cabinet. The fastness of the printed ink to ozone was measured by the difference in the reflectance optical density before and after exposure to ozone.

Reflectance optical density (ROD) measurements were performed using a Gretag® spectrolino spectrophotometer set to the following parameters:

| | |
|---|---|
| Measuring Geometry | 0°/45° |
| Spectral Range | 380-730 nm |
| Spectral Interval | 10 nm |
| Illuminant | D65 |
| Observer | 2° (CIE 1931) |
| Density | Ansi A |
| External Filler | None |

The ozone fastness was quantified by the percentage change in the reflectance optical density of the print. A lower percentage change indicates higher ozone fastness. As an example an ROD percentage change of 5 corresponds to a 5% reduction in the ROD from its starting value after exposure to ozone.

The degree of fade was expressed as $\Delta E$ where a lower figure indicates higher ozone fastness. $\Delta E$ is defined as the overall change in the CIE colour co-ordinates L, a, b of the print and is expressed by the equation $\Delta E = (\Delta L^2 + \Delta a^2 + \Delta b^2)^{0.5}$.

Results

Table 2 below shows the results of ozone fastness tests on the prints made using the three inks. The papers assessed were Canon Professional Photo Paper™ (PR101) and Epson Crispia Paper™.

TABLE 2

| Ink | Compound | PR101 Paper Ozone Fastness | | Crispia Paper Ozone Fastness | |
|---|---|---|---|---|---|
| | | ($\Delta E$) | % change in ROD | ($\Delta E$) | % change in ROD |
| Ink 1 | Example 1 | 2.2 | 5.2 | 3.3 | 2.1 |
| Ink 2 | Example 2 | 1.9 | 3.9 | 3.2 | 2.8 |
| C. Ink 1 | Comparative Dye | 8.6 | 14.0 | 5.4 | 5.6 |

From Table 2 it can be seen that ink Examples 1 and 2 have superior ozone fastness on both papers.

Further Inks

The inks described in Tables A and B may be prepared using the Compounds described in the above Examples 1 to 3. Numbers quoted refer to the number of parts of the relevant ingredient and all parts are by weight. The inks may be applied to paper by ink-jet printing.

The following abbreviations are used in Tables A and B:
PG=propylene glycol
DEG=diethylene glycol
NMP=N-methyl pyrollidone
DMK=dimethylketone
IPA=isopropanol
MeOH=methanol
2P=2-pyrollidone
MIBK=methylisobutyl ketone
P12=propane-1,2-diol
BDL=butane-2,3-diol
CET=cetyl ammonium bromide
PHO=$Na_2HPO_4$
TBT=tertiary butanol
TDG=thiodiglycol

TABLE A

| Example | Dye Content | Water | PG | DEG | NMP | DMK | NaOH | Na Stearate | IPA | MEOH | 2P | MIBK |
|---|---|---|---|---|---|---|---|---|---|---|---|---|
| 1 | 2.0 | 80 | 5 | | 6 | 4 | | | | | 5 | |
| 1 | 3.0 | 90 | | 5 | 5 | | 0.2 | | | | | |
| 1 | 10.0 | 85 | 3 | | 3 | 3 | | | | 5 | 1 | |
| 1 | 2.1 | 91 | | 8 | | | | | | | | 1 |
| 1 | 3.1 | 86 | 5 | | | | | 0.2 | 4 | | | 5 |
| 1 | 1.1 | 81 | | | 9 | | 0.5 | 0.5 | | | 9 | |
| 1 | 2.5 | 60 | 4 | 15 | 3 | 3 | | | 6 | 10 | 5 | 4 |
| 2 | 5 | 65 | | 20 | | | | | 10 | | | |
| 2 | 2.4 | 75 | 5 | 4 | | 5 | | | | 6 | | 5 |
| 2 | 4.1 | 80 | 3 | 5 | 2 | 10 | | 0.3 | | | | |
| 2 | 3.2 | 65 | | 5 | 4 | 6 | | | 5 | 4 | 6 | 5 |
| 2 | 5.1 | 96 | | | | | | | | 4 | | |
| 2 | 10.8 | 90 | 5 | | | | | | 5 | | | |
| 3 | 10.0 | 80 | 2 | 6 | 2 | 5 | | | 1 | | 4 | |
| 3 | 1.8 | 80 | | 5 | | | | | | | 15 | |
| 3 | 2.6 | 84 | | | 11 | | | | | | 5 | |
| 3 | 3.3 | 80 | 2 | | | 10 | | | | 2 | | 6 |
| 3 | 12.0 | 90 | | | | 7 | 0.3 | | 3 | | | |
| 3 | 5.4 | 69 | 2 | 20 | 2 | 1 | | | | | 3 | 3 |
| 3 | 6.0 | 91 | | | 4 | | | | | | 5 | |

TABLE B

| Example | Dye Content | Water | PG | DEG | NMP | CET | TBT | TDG | BDL | PHO | 2P | PI2 |
|---|---|---|---|---|---|---|---|---|---|---|---|---|
| 1 | 3.0 | 80 | 15 | | | 0.2 | | | | | 5 | |
| 1 | 9.0 | 90 | | 5 | | | | | | 1.2 | | 5 |
| 1 | 1.5 | 85 | 5 | 5 | | 0.15 | 5.0 | 0.2 | | | | |
| 1 | 2.5 | 90 | | 6 | 4 | | | | | 0.12 | | |
| 1 | 3.1 | 82 | 4 | 8 | | 0.3 | | | | | | 6 |
| 1 | 0.9 | 85 | | 10 | | | | | 5 | 0.2 | | |
| 1 | 8.0 | 90 | | 5 | 5 | | | 0.3 | | | | |

TABLE B-continued

| Example | Dye Content | Water | PG | DEG | NMP | CET | TBT | TDG | BDL | PHO | 2P | PI2 |
|---|---|---|---|---|---|---|---|---|---|---|---|---|
| 2 | 4.0 | 70 | | 10 | 4 | | | | 1 | | 4 | 11 |
| 2 | 2.2 | 75 | 4 | 10 | 3 | | | | 2 | | 6 | |
| 2 | 10.0 | 91 | | | 6 | | | | | | 3 | |
| 2 | 9.0 | 76 | | 9 | 7 | | 3.0 | | | 0.95 | 5 | |
| 2 | 5.0 | 78 | 5 | 11 | | | | | | | 6 | |
| 2 | 5.4 | 86 | | | 7 | | | | | | 7 | |
| 3 | 2.1 | 70 | 5 | 5 | 5 | 0.1 | 0.2 | 0.1 | 5 | 0.1 | 5 | |
| 3 | 2.0 | 90 | | 10 | | | | | | | | |
| 3 | 2 | 88 | | | | | | 10 | | | | |
| 3 | 5 | 78 | | | 5 | | | 12 | | | 5 | |
| 3 | 8 | 70 | 2 | | 8 | | | 15 | | | 5 | |
| 3 | 10 | 80 | | | | | | 8 | | | 12 | |
| 3 | 10 | 80 | | 10 | | | | | | | | |

The invention claimed is:

1. A compound of Formula (1) or a salt thereof:

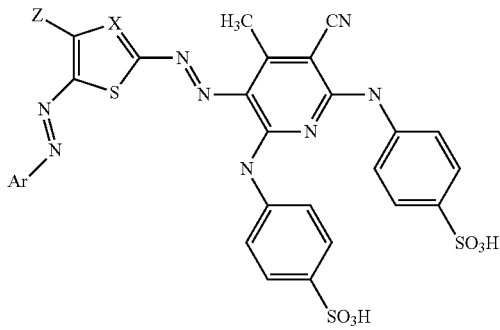

Formula (1)

wherein:

X is N or C(CN);

Z is optionally substituted naphthyl; and

Ar is an aryl group carrying at least one nitro substituent and optionally one or more further substituents.

2. A compound of Formula (1) or a salt thereof according to claim 1 wherein:

(i) Ar has no further substituents; or (ii) Ar has one or more further substituents which are selected from the group consisting of:

optionally substituted alkyl;

optionally substituted alkoxy, optionally substituted aryl, optionally substituted aryloxy, optionally substituted heterocyclyl, polyalkylene oxide, phosphato, sulfo, cyano, halo, ureido, hydroxy, ester, sulfone, —$NR^aR^b$, —$COR^a$, —$CONR^aR^b$, —$NHCOR^a$ and —$SO_2NR^aR^b$, wherein $R^a$ and $R^b$ are each independently H, optionally substituted alkyl, optionally substituted aryl or optionally substituted heteroaryl.

3. A compound of Formula (1) or a salt thereof as claimed in claim 1 wherein Z is unsubstituted naphthyl.

4. A compound of Formula (1) or a salt thereof as claimed in claim 1 wherein Ar is naphthyl carrying at least one nitro substituent and optionally one or more further substituents.

5. A compound of Formula (1) or a salt thereof as claimed in claim 4 wherein:

Ar is a naphthyl group of the Formula:

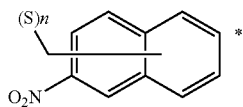

wherein:

each S group independently is an optional substituent;

n is from 1 to 3; and the asterisk (*) represents the point of attachment to the azo linkage in the compound of Formula (1) or a salt thereof.

6. A compound of Formula (1) or a salt thereof as claimed in claim 1 in which the group represented by Ar is substituted with one or more further substituents selected from the group consisting of carboxy and sulfo groups.

7. A compound of Formula (1) or a salt thereof as claimed in claim 1 which is of the Formulae (2) to (4) or a salt thereof:

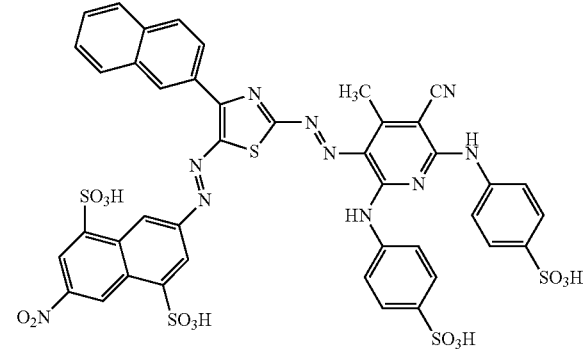

Formula (2)

-continued

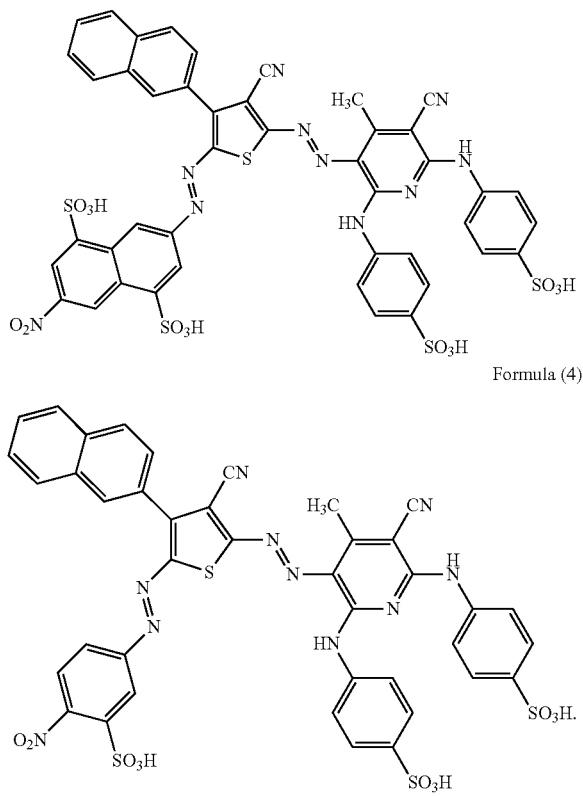

Formula (3)

Formula (4)

8. A composition comprising a compound of Formula (1) or a salt thereof, as claimed in claim 1 and a liquid medium.

9. A composition as claimed in claim 8 which comprises:
(a) from 0.01 to 30 parts of the compound of Formula (1) or a salt thereof; and
(b) from 70 to 99.99 parts of the liquid medium;
wherein all parts are by weight.

10. A composition as claimed in claim 8 wherein the liquid medium comprises a mixture of water and organic solvent or organic solvent free from water.

11. A composition as claimed in claim 8 which is an ink-jet printer ink.

12. A process for forming an image on a substrate comprising ink jet printing an ink-jet printer ink according to claim 11 to the substrate.

13. A material printed with a compound of Formula (1) or a salt thereof according to claim 1.

14. A printed material as claimed in claim 13 which is a print on a photographic quality paper printed by ink jet printing.

15. An ink-jet printer cartridge comprising a chamber and an ink-jet printer ink according to claim 11, wherein the ink is in the chamber.

16. A material printed with a composition according to claim 8.

17. A material printed by means of a process according to claim 12.

* * * * *